United States Patent [19]

Miao

[11] Patent Number: 5,681,728
[45] Date of Patent: Oct. 28, 1997

[54] METHOD AND APPARATUS FOR THE RECOVERY AND PURIFICATION OF ORGANIC ACIDS

[75] Inventor: Fudu Miao, Louisville, Colo.

[73] Assignee: Chronopol, Inc., Golden, Colo.

[21] Appl. No.: 481,753

[22] Filed: Jun. 7, 1995

[51] Int. Cl.⁶ .................................................. C12P 7/40
[52] U.S. Cl. .................... 435/136; 204/519; 204/522; 204/527; 204/530; 204/536; 204/538; 204/534; 204/537; 210/630; 210/637; 210/638; 210/641; 210/651; 210/654; 210/259; 435/137; 435/139; 435/144; 435/145; 435/140; 435/800; 562/486; 562/580; 562/589; 562/593
[58] Field of Search ............................ 435/136, 137, 435/139, 144, 145, 140, 500; 204/527, 534, 538, 530, 519, 522, 537, 536, 630; 562/580, 486, 593, 589; 210/638, 637, 259, 641, 651, 654, 630

[56] References Cited

U.S. PATENT DOCUMENTS

| | | | |
|---|---|---|---|
| 3,619,397 | 11/1971 | Jacquermet | 204/180 |
| 3,704,218 | 11/1972 | Kato et al. | 204/180 |
| 4,110,175 | 8/1978 | Ahlgren et al. | 204/180 |
| 4,698,303 | 10/1987 | Bailey et al. | 435/139 |
| 4,771,001 | 9/1988 | Bailey et al. | 435/139 |
| 4,781,809 | 11/1988 | Falcone | 204/182.4 |
| 4,828,993 | 5/1989 | Sridhar | 435/136 |
| 4,874,700 | 10/1989 | Seipenbusch | 435/145 |
| 4,880,513 | 11/1989 | Davis et al. | 204/182.4 |
| 4,882,277 | 11/1989 | Czytko et al. | 435/136 |
| 4,885,247 | 12/1989 | Datta | 435/139 |
| 5,000,832 | 3/1991 | Steiniger et al. | 204/182.4 |
| 5,002,881 | 3/1991 | Van Nispen et al. | 435/139 |
| 5,006,211 | 4/1991 | Paleologu et al. | 204/182.4 |
| 5,034,105 | 7/1991 | Berglund et al. | 204/182.4 |
| 5,049,250 | 9/1991 | Chlanda | 204/182.4 |
| 5,454,952 | 10/1995 | Brewer | 210/651 |
| 5,460,720 | 10/1995 | Schneider | 210/487 |
| 5,503,729 | 4/1996 | Batchelder et al. | 204/630 |
| 5,503,750 | 4/1996 | Russo et al. | 210/651 |
| 5,505,841 | 4/1996 | Pirbazari et al. | 210/630 |
| 5,522,995 | 6/1996 | Cockrem | 210/637 |

FOREIGN PATENT DOCUMENTS 0 393 818 A1  10/1990  European Pat. Off. .

OTHER PUBLICATIONS

Ohleyer, et al, "Continuous Production of Lactic Acid in a Cell Recycle Reactor", Applied Biochemistry and Biotechnology, vol. 11, pp. 317–332, 1985.

Ohleyer, et al, "Continuous Production of Lactic Acid from Blucose and Lactose and a Cell–Recycle Reactor", Applied Biochemistry and Biotechnology, vol. 11, pp. 457–463, 1985.

Hongo, et al, "Novel Method of Lactic Acid Production by Electrodialysis Fermentation", Applied and Environmental Microbiology, vol. 52, pp. 314–319, 1986.

Srivastave, et al, "Extractive Lactic Acid Fermentation Using Ion–Exchange Resin", Biotechnology and Bioengineering, vol. 39, pp. 607–613, 1992.

Nomura, et al, "Lactic Acid Production by Electrodialysis Fermentation Using Immobilized Growing Cells", Biotechnology and Bioengineering, vol. 30, pp. 788–793, 1987.

Nomura, et al, "Factors Affecting Lactic Acid Production Rate in the Built–in Electrodialysis Fermentation, an Approach to High Speed Batch Culture", Journal of Fermentation and Bioengineering, vol. 71, No. 6, pp. 450–452, 1991.

*Primary Examiner*—Herbert J. Lilling
*Attorney, Agent, or Firm*—Sheridan Ross P.C.

[57] ABSTRACT

The present invention relates to methods and apparatus for reducing the fouling of ion-selective membranes used in the electrodialytic purification of organic acids. More particularly, the present invention relates to the use of nanofiltration and chelating agents for removal of impurities from an organic acid-containing feed material to reduce the fouling of ion-selective membranes used in electrodialysis.

81 Claims, 1 Drawing Sheet

METHOD AND APPARATUS FOR THE RECOVERY AND PURIFICATION OF ORGANIC ACIDS

FIELD OF THE INVENTION

This invention relates to methods for the recovery and purification of organic acid products. In particular, the invention relates to methods and apparatus for the purification and recovery of organic acid products which reduce the fouling of ion-selective membranes used in electrodialysis.

BACKGROUND OF THE INVENTION

Organic acids have many industrial, food, and pharmaceutical uses and are generally produced in technical, food and pharmaceutical grades, depending upon their use. Lactic acid, for example, has been used in the manufacture of adhesives, cleaning and polishing formulations, in the manufacture of textiles, and in the tanning industry for deliming hides. Lactic acid is also a raw material for preparing esters, such as methyl, ethyl and n-butyl lactates which are used as solvents.

Since lactic acid is produced naturally by humans and other animals, lactic acid is considered to be safe for use in food and medical applications. Lactic acid is regularly found in many everyday food products such as milk, yogurt, sauerkraut, pickles and cheese and can be added to a variety of other foodstuffs as a preservative. Lactic acid salts, i.e., lactates such as calcium lactate, can also be used as a nutritional supply. Lactic acid is also used in medical preparations (e.g., as a preservative or pH adjuster) and as a monomer in the manufacture of biodegradable plastics used in sutures, prosthetics, and controlled release drug delivery systems.

Organic acids can be produced either by chemical synthesis or by microbial fermentation. For example, synthetic lactic acid has been manufactured on a commercial scale since 1963, with approximately 50% of the world's lactic acid being produced in this manner. For some applications, "heat-stable" organic acids are particularly desirable. "Heat-stable" organic acids, as used herein, refers to organic acids that do not appreciably change color when heated in sulfuric acid. Heat-stable organic acids, such as lactic acid, have been produced through chemical synthesis because the costs and difficulty in obtaining sufficiently pure lactic acid from microbial fermentation mediums have been prohibitive. However, a number of microorganisms are known to produce valuable organic acids, leading to the possibility of microbially produced organic acid products if appropriate and cost-effective methods can be developed to recover heat-stable organic acids from complex fermentation media.

Electrodialysis is one method that has been used for concentrating and recovering organic acids and their salts. In such a process, acid and base ions in fluids separate from each other across ion-selective membranes in electrodialysis cells when an electric potential is applied to the fluids. Each of U.S. Pat. No. 4,885,247 by Datta, issued Dec. 5, 1989, and European Patent No. 393,818 (EP 393,818) by Glassner et al., issued Oct. 24, 1990, disclose a process in which electrodialysis is utilized to concentrate lactate salts in a fermentation medium, and a subsequent electrodialysis process is utilized to separate the concentrated lactate salt solution into lactic acid and alkali.

One of the drawbacks of electrodialysis is the fouling of the ion-selective membranes, requiring frequent cleaning or replacement of the membranes. For example, the fouling of ion-selective membrane by cellular material in a fermentation medium leads to the need for frequent cleaning (see, for example Hondo et al., "Novel Method of Lactic Acid Production by Electrodialysis Fermentation," *Applied and Environmental Microbiology*, Vol. 52, No. 2, August 1986; Nomura et al., "Lactic Acid Production by Electrodialysis Fermentation Using Immobilized Growing Cells," *Biotechnology and Bioengineering*, Vol. 30, 1987; and U.S. Pat. No. 3,619,397 by Jacquemet, issued Nov. 9, 1971; U.S. Pat. No. 4,781,809 by Falcone, issued Nov. 1, 1988; and U.S. Pat. No. 4,882,277 by Czytko et al., issued Nov. 21, 1989). Fouling of ion-selective membranes can also occur as a result of the proteinaceous and multivalent compounds present in the fermentation medium. In both the '247 U.S. patent by Datta and EP 393,818 by Glassner et al. discussed above, electrodialysis membranes utilized in the concentration step are prone to fouling and require frequent cleaning and/or replacement.

The fouling of ion-selective membranes in electrodialysis results in varying separation efficiencies. Also, the costs of electrodialytic concentration, recovery and purification of organic acids increase with the frequency of replacement of expensive ion-selective membranes. Further, the replacement of ion-selective membranes in electrodialysis cells also requires down time in the production process, resulting in unused capacity and a further loss of efficiency.

Accordingly, it would be desirable to provide a cost efficient method and apparatus for the concentration, recovery and purification of organic acids. It would be desirable to provide a method and apparatus to recover organic acids, such as those produced by microbial fermentation at high yield and having high purity. It would be desirable to provide a cost effective method and apparatus to recover heat stable organic acids.

SUMMARY OF THE INVENTION

In accordance with the present invention a method is provided for the electrodialytic recovery and purification of organic acids and organic acid salts which includes a sequence of steps for removing several types of undesirable impurities from a complex feedstream containing desired organic acids and/or their salts. The benefits of such method are the reduced fouling of electrodialysis membranes, high electrodialysis yield, high electrodialysis efficiency, reduced production of byproducts and the minimization of wastes produced.

More particularly, a method is provided for the recovery and purification of organic acids and organic acid salts which includes the steps of subjecting a feed material having impurities to nanofiltration, and optionally, or alternatively, contacting the feed material with a chelating agent to remove at least a portion of the impurities and subjecting the purified permeate to electrodialysis to produce an organic acid product. Such impurities include, organic material and multivalent compounds. As used herein, the phrase "organic material" can include sugars and proteinaceous materials, both of which are more fully described below.

In one embodiment, the present invention includes a method for recovery and purification of organic acids and organic acid salts by subjecting an impure feed material to nanofiltration to remove at least a portion of the impurities in the impure feed material. In another embodiment, the present invention includes a method for the recovery and purification of organic acids and organic acid salts by contacting a feed material having a multivalent compound concentration with a chelating agent to produce a permeate having a reduced multivalent compound concentration relative to the multivalent compound concentration of the feed material. In another embodiment of the present invention, a method is provided for the recovery and purification of organic acids and organic acid salts comprising the steps of subjecting an impure feed material to nanofiltration to remove at least a portion of the impurities in the feed material, contacting the permeate from the nanofiltration with a chelating agent to remove at least a portion of multivalent compounds remaining in the permeate, and then subjecting the effluent to electrodialysis to produce an organic acid product.

In yet another embodiment of the present invention, a method is provided for the recovery and purification of organic acids produced by fermentation of organic acid-producing microorganisms, which includes subjecting an impure feed material which contains particulate matter, organic material, multivalent compounds and an organic acid salt to microfiltration and/or ultrafiltration to remove at least a portion of the particulate matter from the feed material, then subjecting the permeate to nanofiltration to remove at least a portion of the organic material in the permeate and at least a portion of the multivalent compounds present in the permeate, concentrating the organic acid salt in the resulting liquor to form a concentrated organic salt permeate and subjecting this concentrated organic acid salt permeate to electrodialysis to produce an organic acid product. The method can also include the step of concentrating a waste stream produced from concentration of the organic acid salt in the permeate from nanofiltration to form a concentrated waste stream and a waste depleted stream and discharging at least a portion of the waste depleted stream, and recycling at least a portion of the concentrated waste stream to the fermentor. The method can also include the steps of recycling the retentate of either, or both, the nanofiltration and microfiltration steps.

Another aspect of the present invention is to provide an aqueous solution of an organic acid salt which has been produced by fermentation which contains no greater than about 0.03 wt % sugars, no greater than about 0.05 wt % proteinaceous materials and no greater than about 0.01 wt % multivalent compounds.

Yet another aspect of the present invention is to provide an apparatus for removing impurities from a feed material comprising an organic acid or an organic acid salt, which includes a nanofiltration unit and an electrodialysis unit. Optionally, such apparatus can also include a chelating unit.

DETAILED DESCRIPTION

Figure 1:
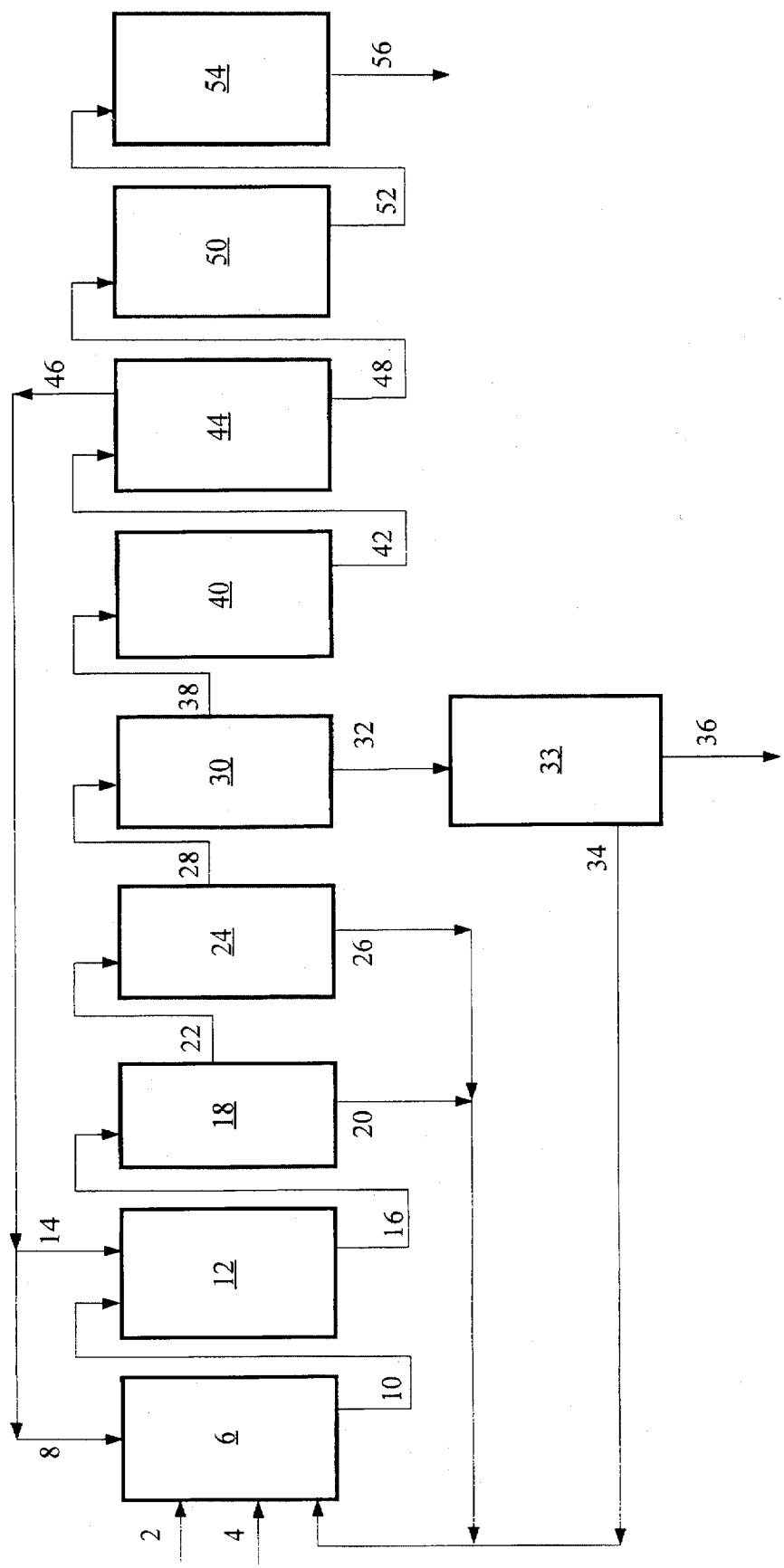
FIG. 1 is a flow diagram of one embodiment of the method for recovery and purification of organic acids according to the present invention.

The present invention includes methods and apparatus for reducing the fouling of ion-selective membranes used in electrodialytic concentration, recovery and purification of organic acids and organic acid salts. More particularly, the present invention includes methods and apparatus for removing compounds from an organic acid and/or organic acid salt-containing feed material which cause the fouling of ion-selective membranes used in electrodialytic concentration, acidification, recovery and purification of such organic acids and organic acid salts.

The methods of the present invention include removal of impurities in an organic acid or organic acid salt-containing feed material by subjecting the feed material to nanofiltration or, alternatively, contacting the feed material with a chelating agent, to remove impurities in the feed material which can foul ion-selective membranes used in electrodialysis. The permeate from such impurity removal steps can be subjected to electrodialysis to obtain an organic acid or concentrated organic acid salt product. In a preferred mode of operation, the present invention includes the removal of impurities by a combination of nanofiltration and chelating of the feed material prior to electrodialysis.

Feed materials suitable for use in connection with the methods and apparatus of the present invention include virtually any feed material which contains one or more organic acids or organic acid salts which can be recovered, purified or concentrated using electrodialysis. Such feed materials include, but are not limited to, fermentation media, vegetable and fruit juices, concentrates and extracts, canning wastes and ion exchange resin regeneration solutions. Preferred for use in the present invention are aqueous fermentation media which contain one or more organic acid salts.

The feed materials suitable for use in the present invention also contain one or more impurities which are capable of fouling membranes used in electrodialysis. Such impurities can include, without limitation, particulate matter, proteinaceous material, multivalent compounds, sugars and mixtures thereof. As used herein, the phrase "particulate matter" refers to particulate matter present in the feed material, such as, microorganisms and cell debris. As used herein, the phrase "proteinaceous materials" refers to proteinaceous matter present in the feed material, such as amino acids and other proteinaceous by-products produced by microorganisms during fermentation. As used herein, the phrase "multivalent compounds" refers to one or more multivalent compounds capable of fouling ion-selective membranes utilized in electrodialysis, and more specifically includes, but is not limited to, divalent metal ions such as zinc, iron, calcium, magnesium, and manganese, and the salts of such metals, including, but not limited to, zinc sulfate, ferric sulfate, calcium sulfate, magnesium sulfate and manganese sulfate.

The feed material also includes any of a number of organic acids and/or organic acid salts which are capable of being recovered, purified or concentrated by electrodialysis. Such feed materials include, but are not limited to, the following organic acids and/or corresponding salts thereof, namely, lactic acid, ascorbic acid, citric acid, maleic acid, fumaric acid, tartaric acid, acetic acid, succinic acid, propionic acid, malic acid, oxalic acid, glycolic acid and mixtures thereof. Preferred for use in the present invention are feed materials which contain lactic acid or lactate salts. Preferred lactate salts include, but are not limited to, ammonium lactate, sodium lactate and potassium lactate. More preferred as a lactate salt is sodium lactate.

In accordance with the present invention, these feed materials can be subjected to nanofiltration using at least one nanofiltration filter material. Such nanofiltration filter materials include, but are not limited to, ceramic membranes, metal membranes, polymer membranes and composite membranes. It is desirable that such membranes are capable of removing from the feed material at least a portion of any multivalent compounds and proteinaceous materials which may be present in the feed material. It is also desirable that the nanofiltration filter material be capable of removing at least a portion of any sugars and polysaccharides that may be present in the feed material. These nanofiltration filter materials can be used in a variety of configurations, including, but not limited to, hollow fiber membranes, tubular membranes and spiral wound membranes. The nanofiltration filter materials useful in the present invention typically have average pore sizes within the range of from about 1 nm to about 5 nm, preferably in the range of from about 1 nm to about 2 nm and more preferably in the range of from about 1 nm to about 1.5 nm.

Although it is not fully understood, it is believed by the inventors that the effectiveness of the nanofiltration filter material to remove impurities such as multivalent compounds and proteinaceous materials is based upon both the pore size characteristics of the nanofiltration filter material and the surface chemistry of the nanofiltration filter material. Accordingly, it is desirable to use a nanofiltration filter material having surface chemistry characteristics which enable the nanofiltration filter material to prevent at least a portion of any multivalent compounds and other charged impurities which may be in the feed material from passing through the membrane during nanofiltration. Preferred for use as nanofiltration filter materials in the present invention are composite membranes which have a negatively charged thin-film separation layer deposited on a base film. It is to be understood, however, that selection of acceptable and preferred nanofiltration filter materials can depend upon the organic acid or organic acid salt being concentrated, purified or separated. Accordingly, preferred for use in the present invention as nanofiltration filter materials when lactic acid or lactic acid salts are being concentrated, purified or separated are materials made of cellulose acetate, polyamides, polyvinyl alcohols, polysulfones, polyether sulfones, polyesters, polyureas, polyamines and ceramics. Even more preferred for use in the present invention as nanofiltration filter materials when lactic acid or lactic acid salts are being concentrated, purified or separated are DESAL-5, obtained from Desalination Systems, Inc., Escondido, Calif. and "FILM-TEC" NF-45 obtained from Dow Chemical, Minneapolis, Minn.

In accordance with the present invention, the feed materials can alternatively or optionally be contacted with at least one chelating agent to remove at least a portion of any multivalent compounds which may be present in the feed material. The chelating agents can be placed in a column, fixed bed, or in any other effective arrangement for being brought into contact with the feed material. As used herein, the phrase "chelating agent" refers to an organic compound which contains two or more electron donor atoms that can form coordinate bonds with metal ions and is capable of selectively removing multivalent compounds from the feed materials described herein. Such chelating agents include, but are not limited to, resins having a macroporous styrene-divinylbenzene matrix and at least one functional group selected from the group consisting of iminodiacetic functional groups, aminophosphonic functional groups and carboxylic functional groups. It is to be understood, however, that selection of acceptable and preferred chelating agents can depend upon the organic acid or organic acid salt being concentrated, purified or separated. Accordingly, preferred for use as chelating agents in the present invention when lactic acid or lactic acid salts are being concentrated, purified or separated are "DUOLITE" C-467 which can be obtained from Rohm & Haas Company, Philadelphia, Pa., "PUROLITE" C105, "PUROLITE" C106, "PUROLITE" S920, "PUROLITE" S930, "PUROLITE" S940 and "PUROLITE" S950, all of which "PUROLITE" products can be obtained from Purolite Company, Bala Cynwyd, Pa.

As stated previously, in a preferred mode of operation the present invention includes the removal of impurities which can foul ion-selective electrodialysis membranes from a feed material by a combination of nanofiltration and chelating. It has been found that the combination of these two steps provides surprising removal of impurities which cannot be achieved through the use of either nanofiltration or chelating individually. In one embodiment of the present invention, a feed material is first subjected to nanofiltration and then contacted with a chelating agent prior to electrodialysis. In another embodiment of the present invention, a feed material is first contacted with a chelating agent and then subjected to nanofiltration prior to electrodialysis. It is preferred, however, that the feed material be subjected to nanofiltration prior to being contacted with a chelating agent because nanofiltration removes impurities from the feed material, such as sugars and proteinaceous material, which can reduce the effectiveness of the chelating agent to remove multivalent compounds.

In accordance with the present invention, the purified organic acid and/or organic acid salt-containing feed material can be subjected to conventional electrodialysis for concentration, or water-splitting bipolar electrodialysis for recovery and/or further purification of the organic acids and their salts. As used herein, the phrase "conventional electrodialysis" refers to the use of an electrodialysis apparatus (i.e. an electrodialysis "cell stack") which does not incorporate water-splitting bipolar membranes. As used herein, the phrase "water-splitting bipolar electrodialysis" refers to the use of an electrodialysis cell stack which incorporates water-splitting bipolar membranes.

In one embodiment of the present invention, conventional electrodialysis is useful for concentrating feed materials which contain organic acids and/or their salts. In another embodiment of the present invention, water-splitting bipolar electrodialysis is useful for recovering an organic acid from its corresponding salt. In another embodiment of the present invention, water-splitting bipolar electrodialysis is useful for recovering a base from its corresponding organic acid salt. In yet another embodiment of the present invention, water-splitting bipolar electrodialysis is useful for recovering both an organic acid and a base from a corresponding organic acid salt.

In general, electrodialysis cell stacks are comprised of two electrodes separated from one another by at least two chambers which are separated from one another by one or more ion-selective membranes, which may or may not be reinforced, depending upon the application. Membranes with high selectivity, high mechanical strength, high capacity and low electrical resistance are preferred. The electrodes are electrically linked to the cell stack chambers by a suitable electrolytic solution. One such suitable electrolytic solution includes sodium sulfate. Ion-selective membranes suitable for use in the present invention include anion-selective, cation-selective and water-splitting bipolar membranes. Suitable anion-selective membranes include, but are not limited to, strongly basic anion-permeable membranes, mono-anion-permeable membranes, homogenous membranes and heterogenous membranes. Preferred for use as anion-selective membranes in the present invention include crosslinked copolymers of styrene and divinylbenzene having fixed quaternary amine groups. More preferred for use as anion-selective membranes in the present invention are membranes comprising "NEOSEPTA" AMX, which are available from Tokuyama Company, Tokuyama, Japan. Suitable cation-selective membranes include, but are not limited to, strongly acidic cation-permeable membranes, mono-cation-permeable membranes, homogenous membranes and heterogenous membranes. Preferred for use as cation-selective membranes in the present invention include crosslinked copolymers of styrene and divinylbenzene having fixed sulfonic groups. More preferred for use as cation-selective membranes in the present invention are membranes comprising "NEOSEPTA" CMX, which are available from Tokuyama Company, Tokuyama, Japan. Suitable water-splitting bipolar membranes include, but are not limited to, composite membranes comprising strongly acidic anion-permeable membranes, mono-anion-permeable membranes, homogenous anion-permeable membranes and heterogenous anion-permeable membranes coupled with strongly basic cation-permeable membranes, mono-cation-permeable membranes, homogenous cation-permeable membranes and heterogenous cation-permeable membranes. Preferred for use as water-splitting bipolar membranes in the present invention include composite membranes consisting of a membrane of a crosslinked copolymer of styrene and divinylbenzene having fixed quaternary amine groups bonded to a membrane of a crosslinked copolymer of styrene and divinylbenzene having fixed sulfonic groups. More preferred for use as water-splitting bipolar membranes in the present invention are composite membranes comprising a membrane of "NEOSEPTA" BP-1 which is available from Tokuyama Company, Tokuyama, Japan.

It is to be understood, however, that selection of acceptable and preferred ion-selective and bipolar membranes, and cell stack arrangements can depend upon the organic acid or organic acid salt being concentrated, purified or separated. According to one embodiment of the present invention, when ammonium lactate is the organic acid salt being converted into lactic acid, it is desirable to use a two-compartment cell stack utilizing water-splitting bipolar membranes and anion-selective membranes. According to another embodiment of the present invention, when sodium lactate is the organic acid salt being converted into lactic acid, it is desirable to use a two-compartment cell stack utilizing water-splitting bipolar membranes and cation-selective membranes. According to yet another embodiment of the present invention, when potassium lactate is the organic acid salt being converted into lactic acid, it is desirable to use a two-compartment cell stack utilizing water-splitting bipolar membranes and cation-selective membranes.

Electrodialysis can be carried out in batch or continuous modes, although batch mode operation is preferred because the conductivity of the feed material which contains the organic acid or organic acid salt can be maintained until nearly the end of the electrodialysis process. In a batch mode of operation, both the feed and the concentrate solutions can be recirculated between the cell stack and storage tanks. The flowrates and temperatures of the organic acid or organic acid salt-containing feed material, the electrolyte and other feed materials, as well as the current density in the electrodialysis cell can be maintained to obtain optimal separation, purification or concentration of the organic acid or organic acid salt. The identification of suitable parameters for operation of the electrodialysis cell stack to obtain optimal separation, purification or concentration of the organic acid or organic acid salt is within the abilities of those of skill in the art, and can be determined without undue experimentation.

Following concentration, recovery or purification of organic acids and/or organic acid salts according to the present invention, the organic acid products can be further treated or "polished" in order to render them suitable for their intended purpose. As used herein, the phrase "organic acid product" refers to both organic acids and their corresponding salts which have been concentrated, recovered or purified according to the methods of the present invention.

In one embodiment, the present invention includes treatment of the organic acid product to obtain a substantially pure or heat stable organic acid. Such treatment includes subjecting the organic acid product to liquid—liquid extraction, ion-exchange or other adsorption process in order to remove at least a portion of any remaining impurities in the organic acid product. Particularly useful are the use of cation and anion resins or mixtures thereof to convert at least a portion of any remaining organic acid salt to its corresponding acid in a purified organic acid product. Also desirable is the use of activated carbon adsorption for the removal of at least a portion of any color bodies and the removal of at least a portion of any remaining proteinaceous material in the organic acid product.

In another embodiment of the present invention, further treatment of the organic acid product includes concentrating the organic acid product such as by evaporation. Such concentrating treatments are particularly useful for providing organic acid products in concentrations required for the production of organic acid-based polymers. For example, lactic acid can be produced at a concentration suitable for use in producing lactide, the cyclic diester of lactic acid, or for use in directly producing higher order oligomers of polylactic acid.

The present invention has several advantages over known processes for the concentration, recovery and purification of organic acids and organic acid salts. According to the methods of the present invention, an organic acid product can be obtained with reduced membrane fouling with respect to known processes. Moreover, such results can be achieved with a total organic acid loss to the recovery system of less than about 5%, preferably less than about 3% and more preferably less than about 1% of the organic acid or organic acid salt present in the feed material.

A further advantage of the present invention is the removal by nanofiltration of sugars, multivalent compounds and proteinaceous materials from fermentation media which contain such impurities along with organic acid salts. In one embodiment of the present invention, nanofiltration of a fermentation medium removes greater than about 30% of the sugars present in the fermentation medium, preferably greater than about 40% of the sugars present in the fermentation medium, and more preferably greater than about 50% of the sugars present in the fermentation medium. In another embodiment of the present invention, nanofiltration of a fermentation medium removes greater than about 60% of the proteinaceous materials present in the fermentation medium, preferably greater than about 70% of the proteinaceous materials present in the fermentation medium, and more preferably greater than about 80% of the proteinaceous materials present in the fermentation medium. In another embodiment of the present invention, nanofiltration of a fermentation medium removes greater than about 70% of the multivalent compounds present in the fermentation medium, preferably greater than about 80% of the multivalent compounds present in the fermentation medium, and more preferably greater than about 90% of the multivalent compounds present in the fermentation medium.

A further advantage of the present invention is the removal of multivalent compounds from fermentation media which contain such impurities along with organic acid salts, by contacting the fermentation media with at least one chelating agent. In one embodiment of the present invention, chelating a fermentation medium according to the present invention removes greater than about 70% of the multivalent compounds present in the feed, preferably greater than about 80% of the multivalent compounds present in the feed, and more preferably greater than about 90% of the multivalent compounds present in the feed.

Yet a further advantage of the present invention is the removal of sugars, multivalent compounds and proteinaceous materials from fermentation media which contain such impurities along with organic acid salts, that can be achieved when the present invention is practiced in a preferred mode of operation, which includes the removal of impurities which can foul ion-selective electrodialysis membranes from a feed material by a combination of nanofiltration and chelating. In a preferred embodiment of the present invention, an aqueous solution of an organic acid salt is provided, such as can be obtained from the concentrating electrodialysis step, which has been produced by fermentation which contains no greater than about 0.03 wt % sugars, no greater than about 0.05 wt % proteinaceous materials and no greater than about 0.01 wt % multivalent compounds.

The methods and apparatus of the present invention will now be described in more detail in relationship to FIG. 1. Although described in relation to the recovery and purification of organic acids produced through microbial fermentation, feed materials containing organic acids which are suitable for recovering and purifying the organic acid according to the methods and apparatus of the present invention are not to be constrained to such fermentation products.

FIG. 1 is a flow diagram of one embodiment of an organic acid recovery and purification process according to the methods and apparatus of the present invention. For convenience, FIG. 1 will be described in relation to the recovery and purification of lactic acid. According to FIG. 1, a fermentation medium 2 and lactic acid-producing microorganisms 4, such as organisms of the genus Lactobacillus are charged to a fermentor 6. The fermentation medium 2 includes a carbohydrate-containing medium suitable for growing lactic acid-producing by the microorganisms 4. Preferably such carbohydrate-containing media is a feedstock which is of low cost such as waste materials from the manufacture of corn products (e.g. corn steep liquor) or from the production of dairy products (e.g. cheese whey hydrolysates), but can also include glucose syrup, molasses, yeast extract, starch and mixtures thereof. The fermentation medium 2 can also contain added sugars and their polymers as a carbon source, including, starches, dextrin, saccharose, maltose, lactose, glucose, fructose, mannose, sorbose, arabinose, xylose, levulose, cellobiose and molasses; fatty acids; and polyalcohols such as glycerine. The fermentation medium 2 can also contain other nutrients, such as a nitrogen source and additional salts and trace metals for growing the lactic acid-producing microorganisms 4.

During the fermentation carried out in the fermentor 6, the pH of the fermentation medium becomes increasingly acidic from the organic acid produced by the organic-acid-producing microorganisms. Accordingly, base 8 is added to the fermentor to control the pH of the fermentation medium to keep it within a range of pH from about pH 5 to about pH 7, which is the preferred pH level for culturing organisms of the genus Lactobacillus. Suitable bases 8 for control of pH include, but are not limited to ammonium hydroxide, sodium hydroxide, potassium hydroxide and mixtures thereof. The addition of base 8 to the fermentor 6 creates a lactate salt in the fermentation medium, such as ammonium lactate, sodium lactate and potassium lactate.

Fermentation in the fermentor 6 can be carried out in a continuous stirred tank reactor in modes such as batch, fed-batch or continuous modes, however it is preferred that the fermentation be carried out in continuous mode as it has a higher productivity. In addition, it is preferred that the fermentor 6 is a cell recycle fermentor such as is described in U.S. Pat. No. 4,698,303 by Bailey et al., issued Oct. 6, 1987 and U.S. Pat. No. 4,771,001 by Bailey et al., issued Sep. 13, 1988, both of which are incorporated herein in their entirety by reference.

As shown in FIG. 1, fermentation medium 10 from the fermentor 6 which contains lactate salt in the range of from about 5% by weight (wt %) to about 15 wt %, preferably in the range of from about 8 wt % to about 15 wt %, and more preferably in the range of from about 10 wt % to about 15 wt % is provided to a pH tank 12 where it is combined with additional base (as previously described) to adjust the pH of the fermentation medium to a pH greater than about pH 8, preferably to a pH of greater than about pH 8.5, and more preferably to a pH of greater than about pH 9, resulting in the precipitation of a substantial portion of the multivalent compounds and proteinaceous materials in the fermentation medium 10. The thus treated fermentation medium 16 can be pumped to a microfiltration (or ultrafiltration) unit 18 where the precipitates can be removed from the permeate using a microfiltration or ultrafiltration filter material or, alternatively, the precipitates can be removed by centrifugation. Microfiltration filter materials suitable for such purposes include polysulfones, cellulose acetate, polypropylenes, polyesters, polyamides and ceramics. The average pore size of such microfiltration filter materials is typically in the range of from about 0.1 micron to about 1 micron and preferably in the range of from about 0.1 micron to about 0.2 micron. Ultrafiltration filter materials suitable for such purposes include polysulfone, cellulose acetate, polypropylene, polyester, polyamide and ceramics. The average pore size of such ultrafiltration filter materials is typically in the range of from about 0.01 micron to about 0.2 micron and preferably in the range of from about 0.05 micron to about 0.1 micron.

The retentate 20 can be recycled back to the fermentor 6. The microfilter permeate 22 can then be provided to a nanofiltration unit 24 where it is subjected to nanofiltration using a nanofiltration filter material as described previously for removing impurities, such as sugars, proteinaceous material, and multivalent compounds. The retentate 26 from nanofiltration unit 24 can be conducted back to the fermentor 6. The permeate 28 from the nanofiltration unit 24 can be conducted to a concentration unit 30. Concentration unit 30 can include, for example, an electrodialysis unit or an evaporator for concentrating the dilute lactic acid salt solution from the nanofiltration step. Typically, after concentrating the lactate salt in concentrating unit 30, the lactate concentration in the resulting liquid is within the range of from about 16 wt % to about 25 wt % lactate, preferably within the range of from about 20 wt % to about 25 wt % lactate, and more preferably within the range of from about 22 wt % to about 25 wt % lactate. Preferably, the concentration unit 30 is a conventional electrodialysis unit, because it allows for the further removal of sugars and proteins present in the nanofiltration permeate 28.

In one embodiment of the present invention, a significant portion of sugars can be removed from the fermentation medium using the recovery methods described herein, including nanofiltration and electrodialysis. In a preferred mode of operation of the present invention, it has been found that greater than about 95% of the sugars can be removed from the fermentation medium using a combination of nanofiltration and electrodialysis, which is advantageous in that it allows the fermentation process to be run continuously without having to substantially completely deplete sugars in the fermentation medium. Accordingly, fermentation media comprising greater than 0.5 g/L sugars, preferably greater than 2 g/L sugars, and more preferably greater than 4 g/L sugars can be utilized as a feed material in the present invention to produce an organic acid product having less than 0.03 wt % sugars, preferably less than 0.01 wt % sugars, and more preferably less than 0.003 wt % sugars.

The concentration unit 30 forms a lactate depleted stream 32, which can be further concentrated, such as through the use of evaporation or reverse osmosis. Preferably, reverse osmosis is used to concentrate the dilute lactate depleted stream which can be recycled 34 back to the fermentor 6. This is particularly advantageous if the recycled stream contains useful nutrients, such as sugars removed from the feed, because it reduces the operational costs for the fermentation step. In addition, reverse osmosis creates a waste depleted stream 36, at least a portion of which can be discharged to the environment, or which can be further treated to remove additional impurities prior to discharge to the environment.

The lactate enriched material obtained from concentration step 30 can be contacted with a chelating agent 40 for removal of multivalent compounds. The chelating agent 40 can be comprised of, for example, as previously described, weak acid resins placed in a column or fixed bed. Alternatively, the permeate from the nanofiltration unit 28 can be contacted with the chelating agent 40 prior to concentration 30 for removing multivalent compounds from the lactate-containing feed material.

The permeate 42 from the chelating step can then be subjected to electrodialysis 44 in order to convert the lactate into lactic acid. Preferably, electrodialysis 44 is bipolar electrodialysis, in which a base 46 is also generated which can be recycled back to the fermentor 6 in order to control the pH of the fermentation medium as previously described. The lactic acid 48 produced from electrodialysis 44 can be further treated, such as by contacting with a strong acid cation exchange resin 50 in order to remove any further residual multivalent compound present in the lactic acid. The permeate from the strong acid cation exchange 52 can be further concentrated 54, such as through the use of an evaporator in order to obtain a lactic acid product 56 having sufficient concentration to be suitable for subsequent use.

One advantage of the methods and apparatus of the present invention is that it is possible to obtain less than about a 1% loss of organic acid or organic acid salt from the original amounts of such compounds in the fermentation medium. This represents a significant savings in organic acids and their salts which are lost in known concentration, recovery and purification processes. Another advantage of the present invention is the reduced fouling of expensive ion-selective membranes used in electrodialysis, which makes electrodialysis a cost competitive concentration, recovery and purification method to obtain an organic acid product. Further, the formation of by-products using electrodialytic concentration, recovery and purification of organic acid products is reduced compared to known processes, making the methods and apparatus of the present invention an environmentally sound solution to the concentration, recovery and purification of organic acids and their salts.

Reference is now made to the following examples, which are intended to illustrate, and not to limit the present invention.

EXAMPLES

Comparative Example 1

The following comparative example illustrates the fouling of ion-selective membranes by impurities in a fermentation medium containing an organic acid salt, sodium lactate, that is concentrated using electrodialysis.

Feed Material Preparation

A fermentation medium having a lactate concentration of 61 g/L was filtered with a 0.1 μm ceramic membrane to obtain a cell-free sodium lactate solution. To remove a portion of the proteinaceous material in the fermentation medium, the solution was then provided to two cascade columns containing activated carbon, each of which were 4.5 cm in internal diameter and 110 cm in height, each loaded with 700 g of activated carbon (12×40 CPG, obtained from Calgon, Pittsburgh, Pa.). Before the adsorption, the activated carbon was soaked for over an hour with distilled water. During the adsorption, the sodium lactate solution flowed downward at a flow rate of 2 bed volumes per hour. The concentration of proteinaceous material in the effluent was measured at 0.26 g/L.

Electrodialysis Cell Stack Arrangement

An electrodialysis cell stack was fabricated which contained 25 cells, each of which consisted of a cation-selective membrane ("NEOSEPTA" CMX) and an anion-selective membrane ("NEOSEPTA" AMX). All of the "NEOSEPTA" membranes were manufactured by Tokuyama Company, Tokuyama, Japan. The electrodes were separated from the cells by NAFION membranes obtained from DuPont, Wilmington, Del. The electrical link between the electrodes and the membranes was a sodium sulfate electrolytic solution. The electrodialysis cell stack was then tested using a synthetic sodium lactate solution to determine whether it was operating properly.

Electrodialysis of the Feed Material

The 50 L carbon-treated sodium lactate solution was then tested in an electrodialysis unit in which the concentrate tank was initially charged with 16 L of 3% synthetic sodium lactate. The electrodialysis stack was operated at a constant current density of 150 amp/m$^2$. The flowrates of both the feed material and the concentrate were controlled at a linear flowrate within the range of from about 5 cm/sec to about 10 cm/sec. The temperature of the electrodialysis process was kept at about 40° C.

Surprisingly, it was found that the membrane voltage increased very rapidly. A few minutes after the beginning of the electrodialysis, it reached maximum voltage setpoint of 2.5 V per cell, and the electrodialysis operation failed completely. The rapid increase in voltage could have indicated either serious membrane fouling or membrane damage.

To exclude the possibility of membrane damage, the membranes were regenerated by washing the cell stack with 0.5N HCl solution by recirculating the solution through the cell stack for 30 minutes. The cell stack was then rinsed with distilled water. The cleaned electrodialysis cell stack was then tested using a synthetic sodium lactate solution to observe how the membrane voltage changed. It was found that the electrodialysis stack worked as well as the previous test runs using the synthetic sodium lactate solution. This confirmed that the membranes had not been damaged (i.e. punctured), and that the rapid voltage increase for the fermentation medium feed material was due to reversible membrane fouling.

Example 2

This example illustrates the effectiveness of nanofiltration in removing multivalent compounds and proteinaceous materials from a fermentation medium feed material containing the organic acid salt ammonium lactate.

A lactate solution was produced by anaerobic fermentation of Lactobacillus cells. The fermentation medium consisted of 10% by volume corn steep water and 90% by volume sweetwater (comprising about 2:1 glucose:fructose with a total sugar concentration of about 6%). The fermentation medium was also supplemented with 50 ppm manganese sulfate. Fermentation was carried out in a 220 L sterilized stainless steel tank at a temperature of 43° C., and the pH of the fermentation medium was controlled during fermentation by the addition of ammonium hydroxide base to maintain the pH of the fermentation medium at pH 6. The fermentation medium was harvested when the lactate concentration was 32 g/L.

The fermentation medium was filtered using a 0.1 µm ceramic filter to remove the cell mass. A five gallon sample of the clarified ammonium lactate solution was sent to Niro Hudson Filtration Co. in Wisconsin for batch nanofiltration trials using Desal-5 and "FILM-TEC" NF-45 nanofiltration membranes simultaneously. The feed was first subjected to nanofiltration using the NF-45 nanofiltration membrane. The permeate was analyzed and the results are set forth in Table 1. The retentate from the NF-45 nanofiltration membrane was then subjected to nanofiltration with a Desal-5 nanofiltration membrane. The experimental results are summarized below in Table 1.

TABLE 1

Experimental Results of Nanofiltration With NF-45 and Desal-5 Nanofiltration Membrane

| SAMPLE | Mg (ppm) | PROTEINS (g/L)* | SAMPLE COLOR |
|---|---|---|---|
| FEED | 181.4 | 1.76 | BROWN |
| NF-45 | 4.4 | 0.38 | COLORLESS |
| Desal-5 | 126.4 | 0.95 | LIGHT BROWN |
| RETENTATE | 642.9 | 10.7 | DEEP BROWN |

*Protein concentrations were determined by the Lowry assay.

From Table 1, it can be calculated that 97% of the multivalent compounds (magnesium) and 79% of the proteinaceous materials were removed by the NF-45 nanofiltration membrane.

Example 3

This example illustrates the effectiveness of nanofiltration in removing multivalent compounds and proteinaceous materials from a fermentation medium feed material containing the organic acid salt sodium lactate.

A clarified sodium lactate solution was prepared according to the fermentation and filtering process described above in Example 2, except that sodium hydroxide rather than ammonium hydroxide was used to control the pH of the fermentation medium. As in Example 2, a batch nanofiltration process with NF-45 membranes was carried out at Niro Hudson Co. in Wisconsin. Samples of both permeate and retentate were taken during the filtration to analyze the concentrations of multivalent compounds (divalent metals and sulfates), proteinaceous materials and sodium lactate.

The nanofiltration trial was carried out at a transmembrane pressure of 320 psig and at a temperature within the range of 43°–44° C. Three plates of NF-45 nanofiltration membranes were used. Table 2 below shows the experimental results for the various trials. The permeate and the retentate were analyzed at different concentrations to determine the nanofiltration filter material's performance. It is noted that in this table, the notation X is used to express the "concentration factor" of the analyzed samples. Accordingly, permeate 2X and retentate 2X represent the permeate and retentate, respectively, when the sample is twice as concentrated as sample 1X, and permeate 4.5X and retentate 4.5X represent the permeate and retentate, respectively, when the sample is 4.5 times as concentrated as sample 1X.

TABLE 2

Experimental Results of Nanofiltration Using NF-45

| SAMPLE | Mg (ppm) | Ca (ppm) | Mn (ppm) | PROTEIN (g/L) | SODIUM LACTATE (g/L) | SULFATE (ppm) | GLUCOSE (g/L) | FLUX (LMH**) | SAMPLE COLOR |
|---|---|---|---|---|---|---|---|---|---|
| PERMEATE 1X | 16.9 | 23.2 | 1.06 | 1.6 | 41.4 | 0 | 1.69 | 21 | COLORLESS |
| RETENTATE 1X | 304.2 | 242.0 | 13.8 | 1.9 | 61.2 | 152 | 1.17 | / | BROWN |
| PERMEATE 2X | 23.4 | 28.4 | 1.54 | 2.2 | 54.2 | 3 | 0.77 | 14 | COLORLESS |
| RETENTATE 2X | 497.2 | 307.6 | 22.0 | 7.9 | 73.9 | /* | 1.51 | / | DEEP BROWN |
| PERMEATE 3X | 38.5 | 39.4 | 1.81 | 2.6 | 64.9 | 37 | 1.58 | 10 | COLORLESS |
| RETENTATE 3X | 691.7 | 345.8 | 30.8 | 10.4 | 82.4 | /* | 2.03 | / | DEEP BROWN |
| PERMEATE 4.5X | 56.6 | 45.0 | 2.83 | 2.8 | 78.8 | 12.6 | 2.79 | 8 | COLORLESS |
| RETENTATE 4.5X | 1022.4 | 397.3 | 54.3 | 15.6 | 94.5 | /* | 2.87 | / | DEEP BROWN |

*The datum was not obtained because of the interference of solution color in the assay.
**LMH represents liter per square meter per hour.

The reported concentrations of the multivalent compounds (divalent metals) were determined by atomic absorption spectrophotometer. Protein concentrations were determined by Kjeldahl method (based on total nitrogen), and sodium lactate concentrations were determined by high pressure liquid chromatography (HPLC). The reported sulfate concentrations were determined by barium sulfate precipitation.

Table 2 shows an excellent rejection of the multivalent compounds (divalent metals and sulfates) and proteinaceous materials by the NF-45 nanofiltration membrane. Approximately a ten-fold reduction of the concentrations of all the major divalent metals and sulfate in the sodium lactate solution was observed after nanofiltration. The membrane rejected approximately 70% to about 80% of the proteinaceous materials present in the feed material. Table 2 also indicates that the NF-45 nanofiltration membrane allows passage of the sodium lactate. More than 80% of the sodium lactate in the feed material passed through the NF-45 nanofiltration membrane.

Example 4

This example illustrates the effect of the use of a chelating agent to remove multivalent compounds from a lactate-containing aqueous feed material.

The removal of multivalent compounds (metal ions) by chelating agents was evaluated using a synthetic sodium lactate solution that contained 60 g/L lactate, 100 ppm calcium and 50 ppm manganese. The chelating agents "PUROLITE" S930, "PUROLITE" S940, "PUROLITE" S950, "PUROLITE" C105, "PUROLITE" C106 and "PUROLITE" C115 were obtained from Purolite Company, Bala Cynwyd, Pa. In the evaluation of each of the chelating agents, 5 g of wet chelating agent were added into a 200 mL sodium lactate solution in a 250 mL shake flask. The flask was then shaken for 24 hours at 37° C. After agitation, the aqueous lactate solution was analyzed to determine the multivalent compound concentrations. The experimental results are shown below in Table 3.

feed material in order to reduce membrane fouling during electrodialysis.

A fermentation medium containing 42.4 g/L lactate (sodium lactate) produced according to the fermentation method described in Example 3 was treated with sodium hydroxide to adjust the pH of the fermentation medium to pH 10.3. The precipitates formed were allowed to settle overnight to obtain a clarified supernatant.

The supernatant was then treated with a chelating agent by providing it to a resin column loaded with 800 g of "PUROLITE" S950 resin obtained from Purolite Company, Bala Cynwyd, Pa. The resin column was 90 cm in height and 4.5 cm in internal diameter. The sodium lactate solution was flowed down through the column at a flow rate of 2.5 L per hour, which corresponds to approximately 2.5 resin bed volumes per hour. A 17 L sodium lactate solution having a brown color was obtained. This solution was then charged to a feed tank for an electrodialysis stack as described previously in Example 1. The concentrate tank for the electrodialysis cell stack was charged with 13 L of a 3% sodium lactate solution. Electrodialysis was carried out in a batch process operated at constant voltage. The experimental conditions and results are summarized below in Table 4.

TABLE 3

| CHELATING AGENT | FUNCTIONAL GROUP OF CHELATING AGENT | INITIAL Ca CONC. | FINAL Ca CONC. | INITIAL Mn CONC. | FINAL Mn CONC. |
|---|---|---|---|---|---|
| S930 | iminodiacetic | 100 ppm | 10.04 ppm | 50 ppm | 1.01 ppm |
| S940 | $Ch_2NHCH_2PO_3$ | 100 ppm | 6.74 ppm | 50 ppm | 0.40 ppm |
| S950 | $CH_2NHCH_2PO_3$ | 100 ppm | 2.32 ppm | 50 ppm | 0.59 ppm |
| C105 | R-COOH | 100 ppm | 5.89 ppm | 50 ppm | 2.11 ppm |
| C106 | R-COOH | 100 ppm | 19.93 ppm | 50 ppm | 1.43 ppm |
| C115 | R-COOH | 100 ppm | 20.63 ppm | 50 ppm | 3.06 ppm |

Example 5

This example illustrates the effect of the use of a chelating agent to remove impurities from a lactic acid-containing

TABLE 4

| Experimental Results for Concentrating Fermented Sodium Lactate | | | |
|---|---|---|---|
| INITIAL LA CONC. IN FEED | 42.4 g/L* | FINAL LA CONC. IN FEED | 2.5 g/L* |

TABLE 4-continued

Experimental Results for Concentrating Fermented Sodium Lactate

| | | | |
|---|---|---|---|
| INITIAL FEED pH | 10.27 | FINAL FEED pH | 8.85 |
| INITIAL FEED CONDUCTIVITY | 27** | FINAL FEED CONDUCTIVITY | 2.5** |
| INITIAL FEED VOLUME | 15.5 L | FINAL FEED VOLUME | 13.5 L |
| INITIAL LA CONC. IN CONCENTRATE | 19.3 g/L* | FINAL LA CONC. IN CONCENTRATE | 60 g/L* |
| INITIAL pH IN CONCENTRATE | 5.89 | FINAL pH IN CONCENTRATE | 9.7 |
| INITIAL CONCENTRATE CONDUCTIVITY | 13.3** | FINAL CONCENTRATE CONDUCTIVITY | 33.4** |
| INITIAL CONCENTRATE VOLUME | 13.5 L | FINAL CONCENTRATE VOLUME | 15.5 L |
| INITIAL STACK CURRENT | 6.0 AMPS | FINAL STACK CURRENT | 1.2 AMPS |
| INITIAL MEMBRANE VOLTAGE | 16.6 V | FINAL MEMBRANE VOLTAGE | 22 V |
| CONSTANT STACK VOLTAGE | 22 V | CURRENT EFFICIENCY | NOT CALCULATED |
| TOTAL ELECTRODIALYSIS TIME | 3 HOURS | LACTATE REMOVAL PERCENTAGE | 94.9% |

*Lactate (LA) concentrations were measured by YSI Biochemistry Analyzer.
**The unit of conductivity is 1000 × microohms/cm.

Table 4 shows that 94.9% of the sodium lactate in the original feed material was removed from the feed material.

Example 6

The following example is another illustration of the effect of use of a chelating agent to reduce membrane fouling during electrodialysis.

A fermentation medium produced according to the fermentation method described in Example 3 having a sodium lactate concentration of 58.7 g/L (lactate) was treated with sodium hydroxide to adjust the pH to 9. The precipitates and cell mass were filtered from the fermentation medium using a 0.1 μm ceramic membrane filter. The permeate obtained contained approximately 60 g/L lactate and was brown in color.

The sodium lactate solution was then contacted with a selective chelating agent, "PUROLITE" S950 obtained from Purolite Company, Bala Cynwyd, Pa., to remove multivalent compounds. The chelating was performed in a column with effective height of 110 cm and an internal diameter of 4.5 cm. The influent was flowed downward at a flowrate of 2 resin bed volumes per hour, and 100 L of effluent were collected.

A batch electrodialysis was performed using a 15 cell electrodialysis cell stack having a construction similar to that described previously in Example 1. A 50 L sample of the sodium lactate solution was charged to the feed tank and the concentrate tank was charged with 10 L of a 3% sodium lactate solution. The experimental conditions and results are summarized in Table 5 below.

TABLE 5

Experimental Results for Electrodialysis of a Sodium Lactate Solution

| | | | |
|---|---|---|---|
| INITIAL LA CONC. IN FEED | 58.7 g/L* | FINAL LA CONC. IN FEED | 4.2 g/L* |
| INITIAL FEED pH | 8.83 | FINAL FEED pH | 6.7 |
| INITIAL FEED CONDUCTIVITY | 25.8** | FINAL FEED CONDUCTIVITY | 3.2** |
| INITIAL FEED VOLUME | 50 L | FINAL FEED VOLUME | 40.6 L |
| INITIAL LA CONC. IN CONCENTRATE | 25.1 g/L* | FINAL LA CONC. IN CONCENTRATE | 148.6 g/L* |
| INITIAL pH IN CONCENTRATE | 6.24 | FINAL pH IN CONCENTRATE | 7.4 |
| INITIAL CONCENTRATE CONDUCTIVITY | 13.8** | FINAL CONCENTRATE CONDUCTIVITY | 39.1** |
| INITIAL CONCENTRATE VOLUME | 10 L | FINAL CONCENTRATE VOLUME | 19.4 L |
| INITIAL STACK VOLTAGE | 22.4 V | FINAL STACK VOLTAGE | 26 V |

TABLE 5-continued

Experimental Results for Electrodialysis of a Sodium Lactate Solution

| | | | |
|---|---|---|---|
| INITIAL MEMBRANE VOLTAGE | 17.0 V | FINAL MEMBRANE VOLTAGE | 22.8 V |
| CURRENT DENSITY | 300 AMP/M$^2$ | CURRENT EFFICIENCY | NOT CALCULATED |
| TOTAL ELECTRODIALYSIS TIME | 11 HOURS | LACTATE REMOVAL PERCENTAGE | 91.9%. |

*Lactate (LA) concentrations were measured by YSI Biochemistry Analyzer.
**The unit of conductivity is 1000 × microohms/cm.

Table 5 shows that this electrodialysis run was successful in that no membrane fouling was observed throughout the run. In addition, the concentrated lactate solution obtained was a light brown color, indicating that at least a portion of the color bodies in the original feed material had been removed through the electrodialysis process.

Example 7

The following example illustrates how organic acids can be separated from an organic acid salt-containing feed material through the use of water-splitting bipolar electrodialysis.

A sodium lactate solution was obtained from fermentation as described previously in Example 3. This fermentation medium was filtered using a 0.1 micron ceramic microfilter to remove particulate matter and contacted with a "PURO-LITE" S950 chelating agent obtained from Purolite Company, Bala Cynwyd, Pa., and conventional electrodialysis. A 52 L sample of the concentrated sodium lactate solution with a lactate concentration of 181.2 g/L was acidified by water-splitting bipolar electrodialysis to see if the sodium lactate could be efficiently converted into lactic acid.

The electrodialysis cell stack used in this acidification experiment contained 5 2-compartment electrodialysis cells, and the compartments of each cell were separated using cation-selective membranes. The cation and bipolar membranes used in the electrodialysis cells were "NEOSEPTA" CMX and "NEOSEPTA" BP-1, respectively, which were manufactured by Tokuyama Company, Tokuyama, Japan.

The water-splitting bipolar electrodialysis unit was operated under the same conditions as the electrodialysis cell stacks in the previous examples. The acidification of the sodium lactate solution was accomplished in batch mode, while the base solution that was obtained was operated in a continuous mode. The sodium hydroxide concentration in the base product tank was maintained at 1.5M by adjusting the flow rate of the distilled water. The results for this example are reported below in Table 6.

TABLE 6

Experimental Results for Acidification of Fermented Sodium Lactate Using Water-Splitting Bipolar Electrodialysis

| | | | |
|---|---|---|---|
| INITIAL LA CONC. IN FEED | 181.2 g/L | FINAL LA CONC. IN FEED | 195.5 g/L* |
| INITIAL FEED pH | 6.21 | FINAL FEED pH | 1.85 |
| INITIAL FEED CONDUCTIVITY | 41.2** | FINAL FEED CONDUCTIVITY | 5.3** |
| INITIAL FEED VOLUME | 52 L | FINAL FEED VOLUME | 45 L |

TABLE 6-continued

Experimental Results for Acidification of Fermented Sodium Lactate Using Water-Splitting Bipolar Electrodialysis

| | | | |
|---|---|---|---|
| INITIAL LA CONC. IN BASE SOLUTION | 0.0 g/L | FINAL LA CONC. IN BASE SOLUTION | 2.32 g/L |
| INITIAL pH OF THE BASE SOLUTION | 12.75 | FINAL pH OF THE BASE SOLUTION | 13.28 |
| INITIAL BASE CONDUCTIVITY | 41.2** | FINAL BASE CONDUCTIVITY | 120.3** |
| INITIAL BASE VOLUME | 18 L | TOTAL BASE VOLUME | 70 L |
| INITIAL STACK VOLTAGE | 15.5 V | FINAL STACK VOLTAGE | 20.5 V |
| INITIAL MEMBRANE VOLTAGE | 8.2 V | FINAL MEMBRANE VOLTAGE | 12.7 V |
| CURRENT DENSITY | 800 AMP/M$^2$ | CURRENT EFFICIENCY | 79% |
| TOTAL ELECTRODIALYSIS TIME | 48 HOURS | LACTATE CONVERSION | 98.1% |

*Lactate (LA) concentrations were measured by HPLC.
**The unit of conductivity is 1000 × microohms/cm.

Table 6 shows that 98.1% of the sodium lactate was converted into lactic acid by water-splitting bipolar electrodialysis.

Example 8

The following example illustrates how electrodialysis removes sugars, e.g., glucose, from fermented solutions containing organic acids.

A batch electrodialysis was performed using a 15 cell electrodialysis stack having a construction similar to that described previously in Example 1. The concentrate tank was operated in a constant volume mode and the lactate concentration was kept approximately constant. The sodium lactate solution obtained by fermentation contained 13.8 g/L glucose. The experimental conditions and results are summarized in Table 7.

TABLE 7

Experimental Conditions and Results of Electrodialysis

| | | | |
|---|---|---|---|
| INITIAL LA CONC. IN FEED | 50.8 g/L* | FINAL LA CONC. IN FEED | 8.16 g/L* |
| INITIAL FEED PH | 8.77 | FINAL FEED PH | 8.42 |
| INITIAL FEED CONDUCTIVITY | 27.1** | FINAL FEED CONDUCTIVITY | 7.1** |
| INITIAL FEED VOLUME | 50 L | FINAL FEED VOLUME | 40 L |
| INITIAL LA CONC. IN CONCENTRATE | 130.5 g/L* | FINAL LA CONC. IN CONCENTRATE | 138.5 g/L* |
| INITIAL PH IN CONCENTRATE | 7 | FINAL PH IN CONCENTRATE | 6.48 |
| INITIAL CONCENTRATE CONDUCTIVITY | 36.6** | FINAL CONCENTRATE CONDUCTIVITY | 40.2** |
| INITIAL CONCENTRATE VOLUME | 16 L | FINAL CONCENTRATE VOLUME | 16 L |
| INITIAL STACK VOLTAGE | 22 V | FINAL STACK VOLTAGE | 27 V |
| INITIAL MEMBRANE VOLTAGE | 15.4 V | FINAL MEMBRANE VOLTAGE | 23.7 V |
| CURRENT DENSITY | 400 AMP/M$^2$ | CURRENT EFFICIENCY | NOT CALCULATED |
| TOTAL ELECTRODIALYSIS TIME | 9 HOURS | LACTATE REMOVAL PERCENTAGE | 78.6% |
| INITIAL GLUCOSE CONC. IN THE FEED | 13.8 g/L* | FINAL GLUCOSE CONC. IN THE FEED | 18.2 g/L* |
| INITIAL GLUCOSE CONC. IN THE CONCENTRATE | 0.55 g/L* | FINAL GLUCOSE CONC. IN THE CONCENTRATE | 1.85 g/L* |
| GLUCOSE REMOVAL PERCENTAGE | 95.1% | | |

*The lactate (LA) and glucose concentrations were measured by YSI Biochemistry Analyzer.
*The unit of the conductivity is 1000 × microohms/cm.

The results listed above in Table 7 indicate that over 95% of the glucose was removed from the feed. Accordingly, this indicates that a high percentage of sugars can be removed using electrodialysis and that electrodialysis can be a good method for removal of uncharged species from a feed.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for the recovery and purification of organic acids produced by fermentation of organic acid-producing microorganisms, the method comprising the steps of:
    (a) subjecting a feed material comprising particulate matter, organic material, a multivalent compound and an organic acid salt to microfiltration to remove at least a portion of said particulate matter, to form a first permeate;
    (b) subjecting said first permeate to nanofiltration with a nanofiltration filter material having an average pore size in the range of from about 1 to about 5 nm to remove at least a portion of said organic material and at least a portion of said multivalent compound from said first permeate to form a second permeate;
    (c) concentrating said organic acid salt in said second permeate to form a concentrated organic acid salt permeate; and
    (d) subjecting said concentrated organic acid salt permeate to electrodialysis to produce an organic acid product.

2. The method as claimed in claim 1, wherein said feed material comprises fermentation medium from a fermenter.

3. The method as claimed in claim 2, wherein said fermenter comprises a cell-recycle fermenter.

4. The method as claimed in claim 2, wherein at least a portion of said particulate matter is returned to said fermenter.

5. The method as claimed in claim 2, wherein said step of concentrating said organic acid salt in said second permeate produces a waste stream, and further comprising the steps of:
    concentrating said waste stream to form a concentrated waste stream and a waste depleted stream;
    discharging at least a portion of said waste depleted stream; and
    conducting at least a portion of said concentrated waste stream to said fermenter.

6. The method as claimed in claim 5, wherein said step of concentrating said waste stream comprises subjecting said waste stream to reverse osmosis.

7. The method as claimed in claim 2, wherein said step of nanofiltration produces a retentate and comprising the further step of conducting said retentate to said fermenter.

8. The method as claimed in claim 2, wherein said step of electrodialysis produces a base product, and comprising the further step of conducting said base product to said fermenter.

9. The method as claimed in claim 2, comprising the further step of contacting said concentrated organic acid salt permeate with a chelating agent to remove at least a portion of any remaining multivalent compound in said concentrated organic acid salt permeate.

10. The method as claimed in claim 9, wherein said chelating agent is selected from the group consisting of resins with a macroporous styrene-divinylbenzene matrix and at least one functional group selected from the group consisting of iminodiacetic functional groups, aminophosphonic functional groups and carboxylic functional groups.

11. The method as claimed in claim 1, wherein said feed material comprises a carbohydrate-containing medium selected from the group consisting of cheese whey hydrolysates, corn steep liquor, glucose syrup, molasses, yeast extract, cellulose, starch, and mixtures thereof.

12. The method as claimed in claim 1, wherein said microfiltration is accomplished with a microfilter material having an average pore size in the range of from about 0.1 micron to about 1 micron.

13. The method as claimed in claim 1, wherein said nanofiltration filter material has an average pore size in the range of from about 1 nm to about 2 nm.

14. The method as claimed in claim 1, wherein said nanofiltration filter material has an average pore size in the range of from about 1 nm to about 1.5 nm.

15. The method as claimed in claim 1, wherein said particulate matter comprises microorganisms and cell debris.

16. The method as claimed in claim 1, wherein said multivalent compound comprises multivalent salts.

17. The method as claimed in claim 1, wherein said multivalent compound is selected from the group consisting of magnesium sulfate, zinc sulfate, manganese sulfate, ferric sulfate, calcium sulfate, and mixtures thereof.

18. The method as claimed in claim 1, wherein said nanofiltration filter material is selected from the group consisting of ceramic membranes, metal membranes, polymer membranes and composite membranes.

19. The method as claimed in claim 1, wherein said nanofiltration filter material comprises a composite membrane having a negatively charged separation layer.

20. The method as claimed in claim 1, wherein said electrodialysis comprises the use of ion-exchange membranes which selectively reject multivalent ions.

21. The method as claimed in claim 1, wherein said electrodialysis comprises water-splitting bipolar electrodialysis.

22. The method as claimed in claim 1, wherein said electrodialysis is selected from the group consisting of two compartment cell stacks and three compartment cell stacks, wherein said compartments are separated by a ion-selective membrane selected from the group consisting of water-splitting bipolar membranes, anion selective membranes and cation selective membranes.

23. The method as claimed in claim 1, wherein said organic acid salt is selected from the group consisting of sodium lactate, potassium lactate and ammonium lactate.

24. The method as claimed in claim 1, wherein said organic material is selected from the group consisting of sugars, proteinaceous material and mixtures thereof.

25. The method as claimed in claim 1, comprising the further step of polishing said organic acid product to obtain a heat stable organic acid product, wherein said polishing is selected from the group consisting of ion-exchange, liquid—liquid extraction and activated carbon adsorption.

26. The method as claimed in claim 25, wherein said heat stable organic acid product comprises heat stable lactic acid.

27. The method as claimed in claim 1, wherein said step of concentrating comprises subjecting said second permeate to electrodialysis.

28. The method as claimed in claim 27, wherein said electrodialysis to concentrate said second permeate comprises conventional electrodialysis.

29. The method as claimed in claim 1, wherein said step of concentrating comprises evaporating at least a portion of said second permeate.

30. The method as claimed in claim 1, comprising the further step of controlling the pH of said feedstream to a pH of greater than about pH 9 to precipitate at least a portion of said organic material and at least a portion of said multivalent compound prior to said step of microfiltration.

31. The method as claimed in claim 1, wherein said feed material comprises organic acid salt in the range of from about 5 wt % to about 15 wt %.

32. The method as claimed in claim 1, wherein said concentrated organic acid salt permeate comprises organic acid salt in the range of from about 16 wt % to about 25 wt %.

33. A method for recovery and purification of an organic acid product, the method comprising the steps of:
(a) subjecting a feed material comprising organic material, a multivalent compound and an organic acid or an organic acid salt to nanofiltration with a nanofiltration filter material to remove at least a portion of said organic material and at least a portion of said multivalent compound to form a permeate;
(b) contacting said permeate with a chelating agent to remove at least a portion of any remaining multivalent compound in said permeate to form an effluent; and
(c) subjecting said effluent to electrodialysis to produce an organic acid product.

34. The method as claimed in claim 33, wherein said feed material comprises fermentation medium from a cell-recycle fermenter.

35. The method as claimed in claim 34, comprising the further steps of:
concentrating said organic acid salt in said permeate with electrodialysis to produce a concentrated organic acid salt permeate and a waste stream;
subjecting said waste stream to reverse osmosis to form a concentrated waste stream and a waste depleted stream;
discharging at least a portion of said waste depleted stream; and
conducting said concentrated waste stream to said fermenter.

36. The method as claimed in claim 34, wherein said step of nanofiltration produces a retentate, and comprising the further step of conducting said retentate to said fermenter.

37. The method as claimed in claim 34, wherein said step of subjecting said effluent to electrodialysis produces a base product, and comprising the further step of conducting said base product to said fermenter.

38. The method as claimed in claim 33, wherein said chelating agent is selected from the group consisting of resins with a macroporous styrene-divinylbenzene matrix and at least one functional group selected from the group consisting of iminodiacetic functional groups, aminophosphonic functional groups and carboxylic functional groups.

39. The method as claimed in claim 33, wherein said feed material comprises a carbohydrate-containing medium selected from the group consisting of cheese whey hydrolysates, corn steep liquor, glucose syrup, molasses, yeast extract, cellulose, starch, and mixtures thereof.

40. The method as claimed in claim 33, wherein said nanofiltration filter material has an average pore size in the range of from about 1 nm to about 5 nm.

41. The method as claimed in claim 40, wherein said nanofiltration filter material has surface chemistry characteristics that prevent multivalent metal ions from passing through said nanofiltration filter material.

42. The method as claimed in claim 33, wherein said nanofiltration filter material has an average pore size in the range of from about 1 nm to about 2 nm.

43. The method as claimed in claim 33, wherein said nanofiltration filter material has an average pore size in the range of from about 1 nm to about 1.5 nm.

44. The method as claimed in claim 33, wherein said multivalent compound comprises multivalent salts.

45. The method as claimed in claim 33, wherein said multivalent compound is selected from the group consisting of magnesium sulfate, zinc sulfate, manganese sulfate, ferric sulfate, calcium sulfate, and mixtures thereof.

46. The method as claimed in claim 33, wherein said nanofiltration filter material is selected from the group consisting of ceramic membranes, metal membranes, polymer membranes and composite membranes.

47. The method as claimed in claim 33, wherein said nanofiltration filter material comprises a composite membrane having a negatively charged separation layer.

48. The method as claimed in claim 33, wherein said electrodialysis comprises conventional electrodialysis.

49. The method as claimed in claim 33, wherein said electrodialysis comprises water-splitting bipolar electrodialysis.

50. The method as claimed in claim 33, wherein said organic acid comprises lactic acid.

51. The method as claimed in claim 33, wherein said organic material is selected from the group consisting of sugars, proteinaceous material and mixtures thereof.

52. The method as claimed in claim 33, comprising the further step of polishing said organic acid product to obtain a heat stable organic acid product, wherein said polishing is selected from the group consisting of ion-exchange, liquid—liquid extraction and activated carbon adsorption.

53. The method as claimed in claim 52, wherein said heat stable organic acid product comprises heat stable lactic acid.

54. The method as claimed in claim 34, comprising the further steps of:
controlling the pH of said feedstream prior to said step of nanofiltration to produce a precipitate comprising at least a portion of said organic material and at least a portion of said multivalent compound; and
subjecting said feedstream to microfiltration to remove at least a portion of said precipitate.

55. The method as claimed in claim 54, comprising the further step of conducting said precipitate removed from said feedstream by microfiltration to said fermenter.

56. The method as claimed in claim 33, wherein said organic acid salt comprises ammonium lactate, said organic acid product comprises lactic acid, and said electrodialysis comprises a two-compartment cell stack having at least one anion-selective membrane.

57. The method as claimed in claim 33, wherein said organic acid salt comprises potassium lactate, said organic acid product comprises lactic acid, and said electrodialysis comprises a two-compartment cell stack having at least one cation-selective membrane.

58. The method as claimed in claim 33, wherein said organic acid salt comprises sodium lactate, said organic acid product comprises lactic acid, and said electrodialysis comprises a two-compartment cell stack having at least one cation-selective membrane.

59. A method for the recovery and purification of an organic acid product from an impure feed material by electrodialysis which reduces the amount of impurities in said feed material which cause fouling of membranes employed in said electrodialysis, the method comprising the steps of:
(a) providing a feed material comprising an organic acid or an organic acid salt, said feed material also having an impurity concentration;
(b) subjecting said feed material to nanofiltration with a filter material to produce a permeate having a reduced impurity concentration relative to said impurity concentration of said feed material; and
(c) subjecting said permeate to electrodialysis to produce an organic acid product.

60. The method as claimed in claim 59, wherein said impurity is selected from the group consisting of particulate matter, sugars, proteinaceous material, multivalent compounds and mixtures thereof.

61. The method as claimed in claim 59, wherein said nanofiltration filter material has an average pore size in the range of from about 1 nm to about 5 nm.

62. The method as claimed in claim 59, wherein said nanofiltration filter material has an average pore size in the range of from about 1 nm to about 2 nm.

63. The method as claimed in claim 59, wherein said nanofiltration filter material has an average pore size in the range of from about 1 nm to about 1.5 nm.

64. The method as claimed in claim 59, wherein said impurity comprises a multivalent compound, and comprising the further step of contacting said permeate with a chelating agent to remove at least a portion of any remaining multivalent compound in said permeate.

65. The method as claimed in claim 64, wherein said chelating agent is selected from the group consisting of resins with a macroporous styrene-divinylbenzene matrix and at least one functional group selected from the group consisting of iminodiacetic functional groups, aminophosphonic functional groups and carboxylic functional groups.

66. The method as claimed in claim 64, wherein said multivalent compound is selected from the group consisting of zinc sulfate, magnesium sulfate, manganese sulfate, ferric sulfate, calcium sulfate, and mixtures thereof.

67. The method as claimed in claim 59, wherein said organic acid comprises lactic acid.

68. The method as claimed in claim 59, wherein said nanofiltration filter material is selected from the group consisting of ceramic membranes, metal membranes, polymer membranes and composite membranes.

69. The method as claimed in claim 59, wherein said nanofiltration filter material comprises a composite membrane having a negatively charged separation layer.

70. The method as claimed in claim 59, wherein said electrodialysis comprises conventional electrodialysis.

71. The method as claimed in claim 59, wherein said electrodialysis comprises water-splitting bipolar electrodialysis.

72. The method as claimed in claim 59, wherein said impurity comprises sugars and said permeate from said nanofiltration step has a sugar concentration of less than about 50% of said sugar concentration in said feed material.

73. The method as claimed in claim 59, wherein said impurity comprises proteinaceous material and said permeate from said nanofiltration step has a proteinaceous material concentration of less than about 80% of said proteinaceous material concentration in said feed material.

74. The method as claimed in claim 59, wherein said impurity comprises multivalent compounds and said permeate from said nanofiltration step has a multivalent compound concentration of less than about 90% of said multivalent compound concentration in said feed material.

75. The method as claimed in claim 59, wherein said impurity comprises sugars and said organic acid product has a sugar concentration of less than about 0.03 wt %.

76. The method as claimed in claim 59, wherein said impurity comprises proteinaceous material and said organic acid product has a proteinaceous material concentration of less than about 0.05 wt %.

77. The method as claimed in claim 59, wherein said impurity comprises multivalent compounds and said organic acid product has a multivalent compound concentration of less than about 0.01 wt %.

78. A method for the recovery and purification of an organic acid product by electrodialysis which reduces the fouling of membranes employed in said electrodialysis, the method comprising the steps of:
- (a) providing a feed material comprising an organic acid or an organic acid salt, said feed material also having a multivalent compound concentration;
- (b) subjecting said feed material to nanofiltration with a nanofiltration filter material having an average pore size in the range of from about 1 nm to about 5 nm to produce a purified feed material;
- (c) contacting said purified feed material with a chelating agent to produce a permeate having a reduced multivalent compound concentration relative to said multivalent compound concentration of said feed material; and
- (d) subjecting said permeate to electrodialysis to produce an organic acid product.

79. The method as claimed in claim 78, wherein said nanofiltration filter material is selected from the group consisting of ceramic membranes, metal membranes, polymer membranes and composite membranes.

80. The method as claimed in claim 78, wherein said nanofiltration filter material comprises a composite membrane having a negatively charged separation layer.

81. A method for the recovery of an organic acid product, the method comprising the steps of:
- (a) culturing organic acid-producing microorganisms to obtain a fermentation medium comprising an organic acid or an organic acid salt and greater than about 0.5 g/L sugars; and
- (b) recovering an organic acid product from said fermentation medium by subjecting said fermentation medium to conventional electrodialysis after nanofiltration wherein said organic acid product comprises less than about 0.03 wt % sugars.

* * * * *